United States Patent
Katra et al.

(10) Patent No.: US 9,687,165 B2
(45) Date of Patent: Jun. 27, 2017

(54) APPARATUS AND METHOD FOR ELECTROCARDIOGRAPHIC MONITORING

(71) Applicant: Greatbatch Ltd., Clarence, NY (US)

(72) Inventors: Rodolphe Katra, Blaine, MN (US); Niranjan Chakravarthy, Eden Prairie, MN (US)

(73) Assignee: Greatbatch Ltd., Clarence, NY (US)

( * ) Notice: Subject to any disclaimer, the term of this patent is extended or adjusted under 35 U.S.C. 154(b) by 544 days.

(21) Appl. No.: 14/215,159

(22) Filed: Mar. 17, 2014

(65) Prior Publication Data
US 2014/0275919 A1 Sep. 18, 2014

Related U.S. Application Data

(60) Provisional application No. 61/786,970, filed on Mar. 15, 2013, provisional application No. 61/787,030, filed on Mar. 15, 2013.

(51) Int. Cl.
| | | |
|---|---|---|
| A61B 5/04 | (2006.01) | |
| A61B 5/042 | (2006.01) | |
| A61B 5/00 | (2006.01) | |
| A61B 5/0432 | (2006.01) | |

(52) U.S. Cl.
CPC .......... *A61B 5/042* (2013.01); *A61B 5/04011* (2013.01); *A61B 5/0422* (2013.01); *A61B 5/0432* (2013.01); *A61B 5/686* (2013.01); *A61B 5/0031* (2013.01)

(58) Field of Classification Search
CPC ..... A61B 5/042; A61B 5/0422; A61B 5/0031; A61B 5/04011
See application file for complete search history.

(56) References Cited

U.S. PATENT DOCUMENTS

| | | | |
|---|---|---|---|
| 8,280,499 B2 | 10/2012 | Brockway et al. | |
| 8,932,221 B2* | 1/2015 | Colliou | A61B 5/0031 600/302 |
| 9,270,025 B2* | 2/2016 | Robertson | A61B 5/0031 |
| 2005/0065445 A1 | 3/2005 | Arzbaecher et al. | |
| 2005/0288600 A1* | 12/2005 | Zhang | A61B 5/0006 600/510 |
| 2006/0095083 A1* | 5/2006 | Zhang | A61N 1/3622 607/14 |

(Continued)

FOREIGN PATENT DOCUMENTS

WO 02/22208 3/2002

OTHER PUBLICATIONS

"EPSearch", 14160341.5, Jul. 1, 2014.

*Primary Examiner* — Tammie K Heller
(74) *Attorney, Agent, or Firm* — Michael P. Horvath

(57) ABSTRACT

In various examples, an apparatus includes an apparatus configured for implantation within a body of a patient. The apparatus, in some examples, includes a housing. At least one antenna extends from the housing, the antenna being flexible such that the antenna conforms to the body of the patient. In some examples, the apparatus includes at least three electrodes, wherein at least a first electrode is disposed on the antenna and at least a second electrode is disposed on the housing. The at least three electrodes are disposed in a non-linear configuration, allowing for differential processing of signals recorded by the at least three electrodes.

20 Claims, 8 Drawing Sheets

(56) References Cited

U.S. PATENT DOCUMENTS

2008/0027515 A1* 1/2008 Harris .................. A61B 5/0031
607/62
2008/0269813 A1 10/2008 Greenhut et al.
2010/0312131 A1 12/2010 Naware et al.
2011/0009712 A1 1/2011 Fayram et al.
2011/0257491 A1* 10/2011 Robertson ............ A61B 5/0031
600/302

* cited by examiner

APPARATUS AND METHOD FOR ELECTROCARDIOGRAPHIC MONITORING

CROSS REFERENCE TO RELATED APPLICATIONS

This application claims the benefit of priority to U.S. Provisional Application Ser. No. 61/786,970, filed on Mar. 15, 2013, entitled "APPARATUS AND METHOD FOR IMPLANTABLE MULTI-VECTOR ELECTROCARDIOGRAPHIC MONITORING," and U.S. Provisional Application Ser. No. 61/787,030, filed on Mar. 15, 2013, entitled "APPARATUS AND METHOD FOR DIFFERENTIAL GAINING AND SENSING IN AN IMPLANTABLE CARDIAC MONITOR," which are incorporated by reference herein in their entireties.

TECHNICAL FIELD

The present patent document pertains generally to cardiac electrophysiologic monitoring and more particularly, but not by way of limitation, to an implantable cardiac monitoring device and method.

BACKGROUND

Electrical signals cause a heart to beat. In a healthy patient, regular heart beats pump blood through the cardiovascular system. The human cardiovascular system is responsible for receiving oxygen-deprived blood into the heart from the venous system of the body, delivering the oxygen-deprived blood to the lungs to be replenished with oxygen, receiving the oxygenated blood from the lungs back into the heart, and delivering the oxygenated blood to the body via the arterial vasculature. This process is regulated within the heart by electrical pulses that control operation of the heart's receiving and pumping chambers.

In a healthy heart, the sinoatrial node of the heart generates electrical pulses in a consistent and regulated fashion to regulate receiving and pumping blood in the heart's chambers. The electrical impulses propagate as activation wavefronts across the atria, the upper chambers of the heart, and cause cells of the atria to depolarize and contract, which forces blood from the atria to the ventricles, the lower chambers of the heart. The ventricles receive the blood from the atria, and the wavefront, after passing through the atrioventricular node and moving to the Purkinje system, moves to cells of the ventricles causing the ventricles to contract and pump the blood to the lungs and to the rest of the body.

Various aspects of cardiac activity (e.g., heart rate, arrhythmias) can be detected by measuring, recording, and analyzing cardiac electrical signals, such as an electrocardiogram (ECG) signal. One way of measuring ECG signals involves attaching electrodes, typically ten, externally to a patient's skin and sensing the electrical signals that form the ECG waveform.

Implantable monitoring systems can be implanted under the skin with electrodes that sense subcutaneous electrical signals, including ECG signals, which are analyzed as being indicative of cardiac activity. In such systems, the electrodes also receive extraneous non-cardiac electrical signal information, which is typically filtered out to produce a more readable ECG. Non-cardiac electrical signals can be generated by muscle tissues during physical activity. In some examples, an implantable loop recorder (ILR) can record and quantify patient heart electrical activity.

OVERVIEW

This overview is intended to provide an overview of subject matter of the present patent application. It is not intended to provide an exclusive or exhaustive explanation of the invention. The detailed description is included to provide further information about the present patent application.

The present inventors have recognized, among other things, that the subject matter can be used to monitor a cardiac parameter. The present inventors have further recognized, among other things, that the subject matter can be used by an implantable device to monitor a cardiac parameter. To better illustrate the apparatuses and methods described herein, a non-limiting list of examples is provided here:

Example 1 can include subject matter that can include an apparatus configured for implantation within a body of a patient. The apparatus includes a housing. At least one antenna extends from the housing. The antenna is flexible such that the antenna conforms to the body of the patient. At least three electrodes include at least a first electrode disposed on the antenna and at least a second electrode disposed on the housing, wherein the at least three electrodes are disposed in a non-linear configuration.

In Example 2, the subject matter of Example 1 is optionally configured such that the at least one antenna includes at least two electrodes.

In Example 3, the subject matter of Example 2 is optionally configured such that the at least two electrodes of the antenna are configured to measure a local signal and the first electrode and the second electrode are configured to measure a global signal.

In Example 4, the subject matter of any one of Examples 1-3 optionally includes a header attached to the housing, wherein the at least one antenna is coupled to the header.

In Example 5, the subject matter of Example 4 is optionally configured such that at least a third electrode is disposed on the header.

In Example 6, the subject matter of any one of Examples 1-5 is optionally configured such that the at least three electrodes provide at least three vectors along which to sense a physiologic parameter.

In Example 7, the subject matter of Example 6 is optionally configured such that the physiologic parameter includes a cardiac parameter.

In Example 8, the subject matter of Example 7 is optionally configured such that the cardiac parameter includes an electrocardiogram (ECG) signal.

In Example 9, the subject matter of Example 8 optionally includes circuitry configured to use the at least three vectors to gain or subtract a first portion of the ECG signal and amplify a remaining second portion of the ECG signal.

In Example 10, the subject matter of Example 8 optionally includes circuitry configured to use the at least three vectors to determine a local signal and a global signal, the circuitry being configured to subtract the local signal from the global signal to lessen an amount of noise present in the ECG signal.

Example 11 can include, or can optionally be combined with any one of Examples 1-10 to include subject matter that can include a system including an implantable device configured for implantation within a body of a patient. The device includes a housing. At least one antenna extends from the housing. The antenna is flexible such that the antenna conforms to the body of the patient. At least three electrodes include at least a first electrode disposed on the antenna and at least a second electrode disposed on the housing, wherein the at least three electrodes are disposed in a non-linear configuration.

In Example 12, the subject matter of Example 11 is optionally configured such that the at least three electrodes provide at least three vectors along which to sense an electrocardiogram (ECG) signal.

In Example 13, the subject matter of Example 12 optionally includes circuitry configured to use the at least three vectors to gain or subtract a first portion of the ECG signal and amplify a remaining second portion of the ECG signal.

In Example 14, the subject matter of Example 12 optionally includes circuitry configured to use the at least three vectors to determine a local signal and a global signal, the circuitry being configured to subtract the local signal from the global signal to lessen an amount of noise present in the ECG signal.

In Example 15, the subject matter of Example 12 optionally includes an external device communicatively coupled to the implantable device. The external device is configured to use the at least three vectors to gain or subtract a first portion of the ECG signal and amplify a remaining second portion of the ECG signal.

In Example 16, the subject matter of Example 12 optionally includes an external device communicatively coupled to the implantable device. The external device is configured to use the at least three vectors to determine a local signal and a global signal. The circuitry is configured to subtract the local signal from the global signal to decrease an amount of noise present in the ECG signal.

In Example 17, the subject matter of any one of Examples 11-16 is optionally configured such that the implantable device includes a header attached to the housing, wherein the at least one antenna is coupled to the header.

In Example 18, the subject matter of Example 17 is optionally configured such that at least a third electrode is disposed on the header.

In Example 19, the subject matter of any one of Examples 11-18 is optionally configured such that the at least one antenna includes at least two electrodes.

In Example 20, the subject matter of Example 19 is optionally configured such that the at least two electrodes of the antenna are configured to measure a local signal and the first electrode and the second electrode are configured to measure a global signal.

In Example 21, the subject matter of any one of Examples 1-20 is optionally configured such that the at least one antenna includes at least two antennas extending from the housing.

In Example 22, the subject matter of Example 21 is optionally configured such that the at least two antennas include three antennas extending from the housing.

In Example 23, the subject matter of Example 21 is optionally configured such that the at least two antennas include different lengths from one another.

In Example 24, the subject matter of Example 21 is optionally configured such that each of the at least two antennas includes at least two electrodes.

In Example 25, the subject matter of any one of Examples 1-24 is optionally configured such that the at least three electrodes are conformal to a patient torso and disposed in the non-linear configuration.

DETAILED DESCRIPTION

Figure 1:
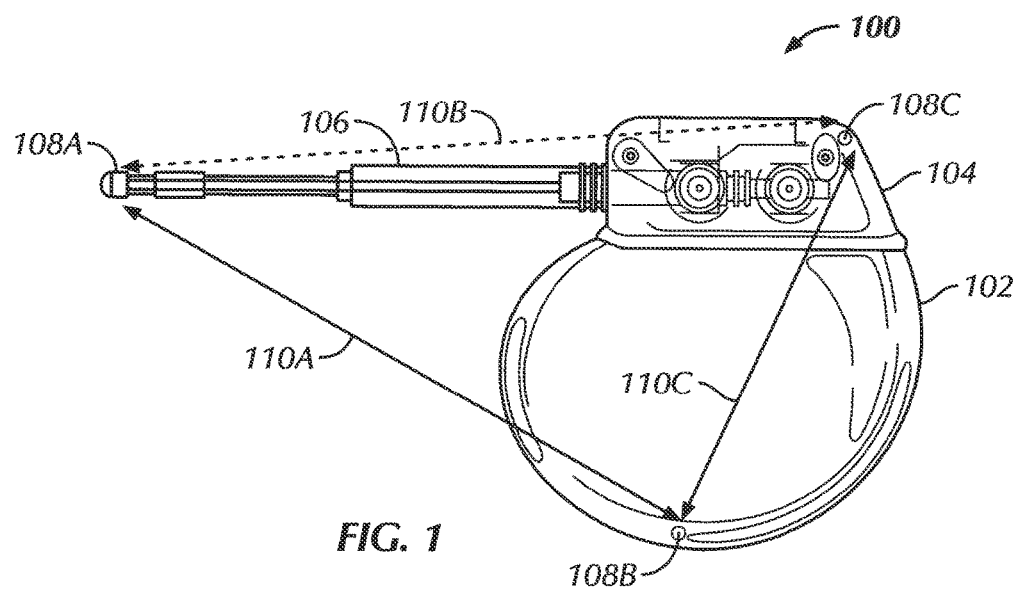
FIG. 1 shows a multi-vector implantable apparatus in accordance with at least one example of the invention.

The present patent application relates to apparatuses, systems, algorithms, and methods for monitoring a physiological parameter, such as, but not limited to, a cardiac parameter. For instance, the apparatuses, systems, algorithms, and methods of the present patent application are used, in some examples, to measure a cardiac parameter in an implantable device. In some examples, the apparatuses, systems, algorithms, and methods are configured to provide an output differential signal. In some examples, the output differential signal is tailored to decrease and/or amplify one or more signal features.

The present inventors have recognized, among other things, that it is desirable to have a multivector implantable loop recorder (ILR) to allow for vector selection to improve detection ability of the ILR and to allow for improved sensing. The present inventors have further recognized, among other things, that it is desirable to have a multivector implantable loop recorder (ILR) to allow for differential signal processing of data collected from multiple electrode pairs. It should be understood, however, that the subject matter described herein can be used with other implantable medical devices, as well as an external monitor or device in some examples.

Currently, existing ILRs have a single vector for cardiac sensing created by in-line electrodes. Implantable medical devices that have only two electrodes or have the electrodes arranged in-line are typically only capable of sensing electric signal in a single vector. The vector of detection is determined by the orientation of the implanted ILR. Such a single-vector ILR has a relatively limited detection ability due to the linear arrangement of the electrodes and the lack of multiple electrodes. In many cases, electric signals, especially subcutaneous ones, have a limited detection ability and resolution. This can be a major limitation for the detection of aberrant atrial activity and diagnosis of atrial fibrillation, as well as being significantly prone to noise and artifact due to the proximity of the electrodes. Having a multi-vector ILR allows for vector selection to improve detection ability of the ILR and allows for improved sensing.

In various examples, the present document describes a device including multiple electrodes arranged in a configuration that is not linear, thereby allowing for multi-vector planar electrocardiography. Various configurations of multiple electrodes are contemplated herein. For instance, in some examples, the electrode pairs that comprise the detection vector can be selected to create the desired vector and orientation. In some examples, all the electrode pairs are active serially or simultaneously with the data collected, stored, or transmitted for processing. In some examples, the electrodes can be tethered to the device body with flexible leads that are amenable for site-specific placement by the implanting physician.

In some examples, an ILR includes three or more electrodes that would allow a multi-vector interrogation of cardiac activity. In some examples, these electrodes would be arranged in different configurations to replicate common vectors of a twelve-lead vector electrocardiographic system. In various examples, the electrodes can be planar or three-dimensional, for instance, enabled by electrode extensions.

In various examples, multiple vectors can be used to obtain different "directional" views of the heart (e.g., Lead I and Lead II). In contrast to classic lead placement techniques, the arrangement of electrodes in an implanted medical device is constrained by available device space. Hence, in some examples, device-specific electrode arrangements can be used to obtain device-specific views of the heart and also be transformed to the traditional twelve-lead view. In various examples, the present description relates to a device with multiple electrodes arranged in a configuration that is not linear, thereby allowing for differential signal processing of data collected from multiple body-conforming electrode pairs.

Referring to FIG. 1, in some examples, an apparatus 100 is configured for implantation within a body of a patient. In some examples, the apparatus 100 includes an implantable loop recorder (ILR). In some examples, the apparatus 100 can include another type of implantable device. In some examples, the apparatus 100 includes a housing 102. In some examples, the housing 102 is formed from a biocompatible material. In various examples, the housing 102 is formed from a metallic material, a polymeric material, a ceramic material, or the like. The apparatus 100, in some examples, includes an elongate member, such as, for instance, at least one antenna 106, extending from the housing 102. In some examples, the antenna 106 is flexible such that the antenna 106 conforms to the body of the patient. However, in other examples, the antenna 106 can be partially or completely rigid. In some examples, the apparatus 100 need not necessarily include an antenna and can include another elongate member extending from the housing 102, such as, for example, a lead, a tube, a rod, or a protrusion, to name a few.

In some examples, the apparatus 100 includes a header 104. In some example, the header 104 is configured for attachment of the antenna 106 or other elongate member. In some examples, the header 104 provides a biocompatible and hermetically sealed connection between the antenna 106 (or other elongate member) and circuitry, one or more modules, or one or more electronic components within the housing 102. That is, in some examples, the at least one antenna 106 (or other elongate member) is coupled to the header 104 to provide electrical engagement between the at least one antenna 106 and the circuitry, or more modules, or one or more electronic components within the housing 102.

In some examples, the apparatus 100 includes at least three electrodes 108. In some examples, at least a first electrode 108A is disposed on the antenna 106 and at least a second electrode 108B is disposed on the housing 102. In some examples, the housing 102 is formed from a conductive material, such that the entire housing 102 acts as the second electrode 108B. In other examples, the housing 102 is formed from a conductive material and includes a non-conductive and/or insulating coating or other covering around the housing 102 but leaving at least one uninsulated area to act as the second electrode 108B. In some examples, the housing 102 includes more than one uninsulated area to act as more than one electrode. In some examples, the housing 102 is formed from a non-conductive material or is completely covered or coated with a non-conductive and/or insulating material and one or more electrodes are affixed or otherwise attached to the housing 102 to form at least the second electrode 108B. In some examples, the housing 102 is at least partially coated with a parylene coating, for instance. In some examples, at least a third electrode 108C is disposed on the header 104. In some examples, the electrodes 108 of the apparatus 100 include the first electrode 108A at a tip of the antenna 106, the second electrode 108B at a base of the housing 102, and the third electrode 108C at a corner of the header 104. In some examples, the apparatus 100 can include fewer than three electrodes. In other examples, the apparatus 100 can include more than three electrodes. Although shown in FIG. 1 with one electrode 108 on the antenna 106, in some examples, it is contemplated that the antenna can include more than one electrode.

In some examples, the at least three electrodes 108 are disposed in a non-linear configuration. In some examples, as seen in FIG. 1, the first, second, and third electrodes 108A, 108B, 108C generally form a triangle when viewed as shown in FIG. 1, such that three distinct vectors 110 are formed between electrode pairs formed by the first, second, and third electrodes 108A, 108B, 108C. In some examples, the three electrodes 108A, 108B, 108C form the basic Lead I, II, III triangle (Einthoven triangle).

In some examples, the at least three electrodes 108 form at least three vectors 110 along which to sense a physiologic parameter. In some examples, the physiologic parameter includes a cardiac parameter. In further examples, the cardiac parameter includes an electrocardiogram (ECG) signal. In some examples, a first vector 110A is formed between the first electrode 108A and the second electrode 108B, a second vector 110B is formed between the first electrode 108A and the third electrode 108C, and a third vector 110C is formed between the second electrode 108B and the third electrode 108C. In some examples, since a separation between the second electrode 108B and the third electrode 108C is smaller than a separation between the first electrode 108A and the second electrode 108B, a signal from the electrode pair including the second electrode 108B and the third electrode 108C can be dynamically amplified to match a lead amplitude of a signal of the electrode pair including the first electrode 108A and the second electrode 108B. In some examples, the antenna 106 can include a length allowing for a vector configuration, such that the signal from the electrode pair including the second electrode 108B and the third electrode 108C need not be amplified.

Figure 2:
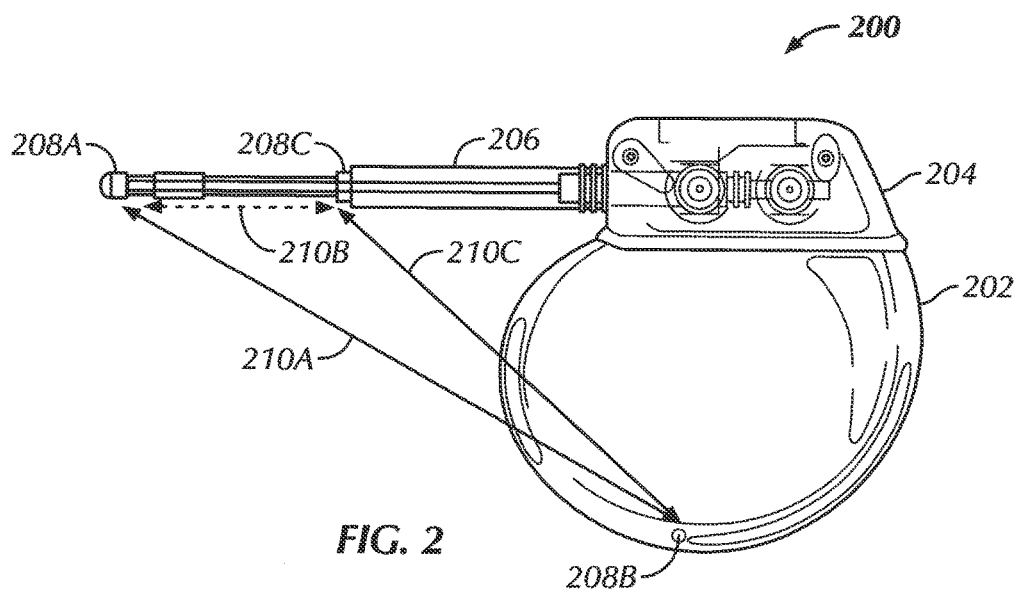
FIG. 2 shows a multi-vector implantable apparatus in accordance with at least one example of the invention.

Referring to FIG. 2, in some examples, an apparatus 200 is configured for implantation within a body of a patient. In some examples, the apparatus 200 is similar to the apparatus 100 described herein. In some examples, the apparatus 200 includes an implantable loop recorder (ILR). In some examples, the apparatus 200 can include another type of implantable device. In some examples, the apparatus 200 includes a housing 202. In some examples, the housing 202 is formed from a biocompatible material. In various examples, the housing 202 is formed from a metallic material, a polymeric material, a ceramic material, or the like. The apparatus 200, in some examples, includes an elongate member, such as, for instance, at least one antenna 206, extending from the housing 202. In some examples, the antenna 206 is flexible such that the antenna 206 conforms to the body of the patient. However, in other examples, the antenna 206 can be partially or completely rigid. In some examples, the apparatus 200 need not necessarily include an antenna and can include another elongate member extending from the housing 202, such as, for example, a lead, a tube, a rod, or a protrusion, to name a few.

In some examples, the apparatus 200 includes a header 204. In some examples, the header 204 is configured for attachment of the antenna 206 or other elongate member. In some examples, the header 204 provides a biocompatible and hermetically sealed connection between the antenna 206 (or other elongate member) and circuitry, one or more modules, or one or more electronic components within the housing 202. That is, in some examples, the at least one antenna 206 (or other elongate member) is coupled to the header 204 to provide electrical engagement between the at least one antenna 206 and the circuitry, one or more modules, or one or more electronic components within the housing 202.

In some examples, the apparatus 200 includes at least three electrodes 208. In some examples, at least a first electrode 208A is disposed on the antenna 206 and at least a second electrode 208B is disposed on the housing 202. In some examples, the housing 202 is formed from a conductive material, such that the entire housing 202 acts as the second electrode 208B. In other examples, the housing 202 is formed from a conductive material and includes a non-conductive and/or insulating coating or other covering around the housing 202 but leaving at least one uninsulated area to act as the second electrode 208B. In some examples, the housing 202 includes more than one uninsulated area to act as more than one electrode. In some examples, the housing 202 is formed from a non-conductive material or is completely covered or coated with a non-conductive and/or insulating material and one or more electrodes are affixed or otherwise attached to the housing 202 to form at least the second electrode 208B. In some examples, the housing 202 is at least partially coated with a parylene coating, for instance. In some examples, at least a third electrode 208C is also disposed on the antenna 206. That is, the at least one antenna 206 includes at least two electrodes 208, such as, for instance, the first and the third electrodes 208A, 208C. In some examples, the electrodes 208 of the apparatus 200 include the first electrode 208A at a tip of the antenna 206, the second electrode 208B at a base of the housing 202, and the third electrode 208C at a location on the antenna between the tip of the antenna 206 and the header 204. In some examples, the apparatus 200 can include fewer than three electrodes. In other examples, the apparatus 200 can include more than three electrodes.

In some examples, the at least three electrodes 208 form at least three vectors 210 along which to sense a physiologic parameter. In some examples, the physiologic parameter includes a cardiac parameter. In further examples, the cardiac parameter includes an electrocardiogram (ECG) signal. In some examples, a first vector 210A is formed between the first electrode 208A and the second electrode 208B, a second vector 210B is formed between the first electrode 208A and the third electrode 208C, and a third vector 210C is formed between the second electrode 208B and the third electrode 208C.

In some examples, the at least three electrodes 208 are disposed in a non-linear configuration. In some examples, as seen in FIG. 2, the first, second, and third electrodes 208A, 208B, 208C generally form a triangle when viewed as shown in FIG. 2, such that the at least three distinct vectors 210 are formed between electrode pairs formed by the first, second, and third electrodes 208A, 208B, 208C. In some examples, the three electrodes 208A, 208B, 208C approximate the basic Lead I, II, III triangle (Einthoven triangle). In some examples, the two solid lines of FIG. 2 indicate two measured vectors, the first vector 210A and the third vector 210C. In some examples, the first vector 210A can be considered a Lead II. However, the third vector 210C is not a traditional electrode configuration. In various examples, an estimated vector, the second vector 210B (shown in FIG. 2 as a dashed line), is obtained as the difference between the first and third vectors 210A, 210C, which are each measured. In some examples, the estimated second vector 210B is similar to a traditional Lead I, and can be dynamically amplified to match the Lead II (the first vector 210A) measurement. In some examples, the at least two electrodes 208A, 208C of the antenna 206 are configured to measure a local signal and the first electrode 208A and the second electrode 208B are configured to measure a global signal. For instance, the second vector 210B can be used to measure a local bipolar signal and/or compared to a more far-field electrode vector, such as the first vector 210A and/or the third vector 210C.

Figure 3:
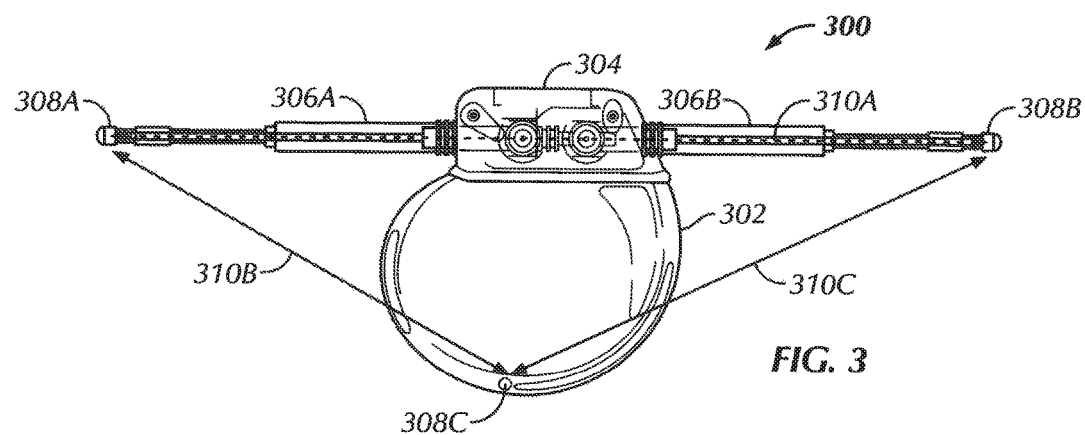
FIG. 3 shows a multi-vector implantable apparatus in accordance with at least one example of the invention.

Referring to FIG. 3, in some examples, an apparatus 300 is configured for implantation within a body of a patient. In some examples, the apparatus 300 is similar to the apparatuses 100, 200 described herein. In some examples, the apparatus 300 includes an implantable loop recorder (ILR). In some examples, the apparatus 300 can include another type of implantable device. In some examples, the apparatus 300 includes a housing 302. In some examples, the housing 302 is formed from a biocompatible material. In various examples, the housing 302 is formed from a metallic material, a polymeric material, a ceramic material, or the like. The apparatus 300, in some examples, includes at least two elongate members, such as, for instance, at least two antennas 306, extending from the housing 302. In some examples, the apparatus 300 includes a first antenna 306A and a second antenna 306B. In some examples, one or both of the at least two antennas 306 are flexible such that the one or more antennas 306 conform to the body of the patient. However, in other examples, one or both of the at least two antennas 306 can be partially or completely rigid. In some examples, the apparatus 300 need not necessarily include one or both of the at least two antennas and can include another elongate member extending from the housing 302 instead of one or both of the at least two antennas, such as, for example, a lead, a tube, a rod, or a protrusion, to name a few. In some examples, the at least two antennas 306 include different lengths from one another. In other examples, the at least two antennas 306 include similar lengths to one another.

In some examples, the apparatus 300 includes a header 304. In some examples, the header 304 is configured for attachment of the at least two antennas 306 or other elongate members. In some examples, the first antenna 306A and the second antenna 306B extend from the header 304 generally in line with one another. In other examples, the first antenna 306A and the second antenna 306B extend from the header 304 offset from one another, for instance, stacked one on top of the other, next to each other, or otherwise offset. In some examples, the header 304 provides a biocompatible and hermetically sealed connection between the at least two antennas 306 (or other elongate members) and circuitry, one or more modules, or one or more electronic components within the housing 302. That is, in some examples, the at least two antennas 306 (or other elongate members) are coupled to the header 304 to provide electrical engagement between the at least two antennas 306 (or other elongate members) and the circuitry, one or more modules, or one or more electronic components within the housing 302.

In some examples, the apparatus 300 includes at least three electrodes 308. In some examples, at least a first electrode 308A is disposed on the first antenna 306A, at least a second electrode 308B is disposed on the second antenna 306B, and at least a third electrode 308C is disposed on the housing 302. In some examples, the housing 302 is formed from a conductive material, such that the entire housing 302 acts as the third electrode 308C. In other examples, the housing 302 is formed from a conductive material and includes a non-conductive and/or insulating coating or other covering around the housing 302 but leaving at least one uninsulated area to act as the third electrode 308C. In some examples, the housing 302 includes more than one uninsulated area to act as more than one electrode. In some examples, the housing 302 is formed from a non-conductive material or is completely covered or coated with a non-conductive and/or insulating material and one or more electrodes are affixed or otherwise attached to the housing 302 to form at least the third electrode 308C. In some examples, the housing 302 is at least partially coated with a parylene coating, for instance. In some examples, the electrodes 308 of the apparatus 300 include the first electrode 308A at a tip of the first antenna 306A, the second electrode 308B at a tip of the second antenna 306B, and the third electrode 308C at a base of the housing 302. In some examples, the apparatus 300 can include fewer than three electrodes. In other examples, the apparatus 300 can include more than three electrodes. Although shown in FIG. 3 with one electrode 308 on each the antennas 306, in some examples, it is contemplated that one or both of the antennas can include more than one electrode.

In some examples, the at least three electrodes 308 are disposed in a non-linear configuration. In some examples, as seen in FIG. 3, the first, second, and third electrodes 308A, 308B, 308C generally form a triangle when viewed as shown in FIG. 3, such that three distinct vectors 310 are formed between electrode pairs formed by the first, second, and third electrodes 308A, 308B, 308C. In some examples, the three electrodes 308A, 308B, 308C form the basic Lead I, II, III triangle (Einthoven triangle).

In some examples, the at least three electrodes 308 form at least three vectors 310 along which to sense a physiologic parameter. In some examples, the physiologic parameter includes a cardiac parameter. In further examples, the cardiac parameter includes an electrocardiogram (ECG) signal. In some examples, a first vector 310A is formed between the first electrode 308A and the second electrode 308B, a second vector 310B is formed between the first electrode 308A and the third electrode 308C, and a third vector 310C is formed between the second electrode 308B and the third electrode 308C.

Figure 4:
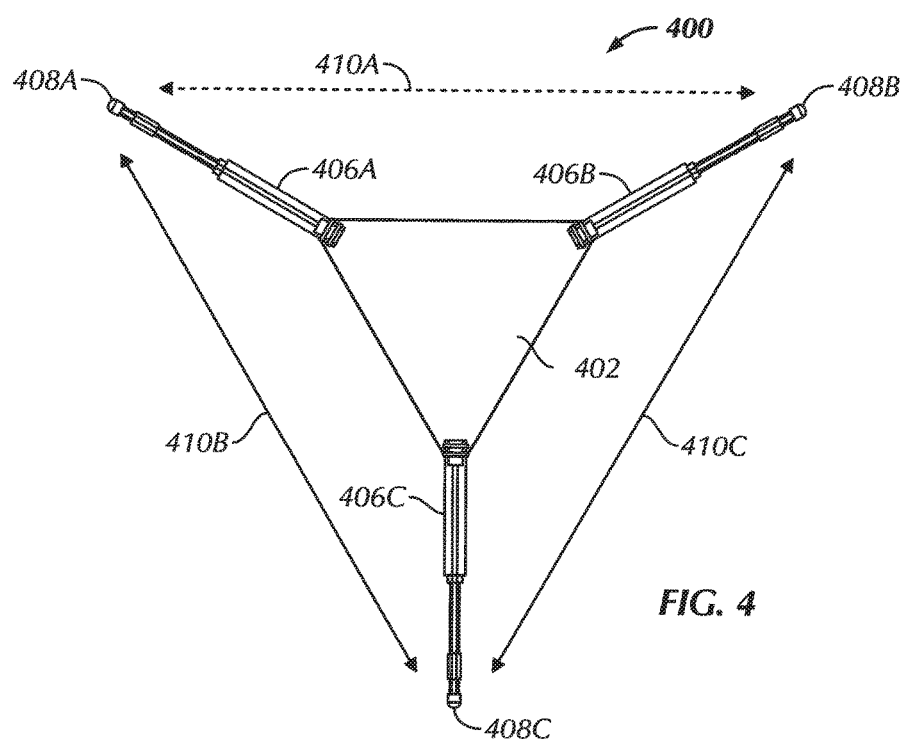
FIG. 4 shows a multi-vector implantable apparatus in accordance with at least one example of the invention.

Referring to FIG. 4, in some examples, an apparatus 400 is configured for implantation within a body of a patient. In some examples, the apparatus 400 is similar to the apparatuses 100, 200, 300 described herein. In some examples, the apparatus 400 includes an implantable loop recorder (ILR). In some examples, the apparatus 400 can include another type of implantable device. In some examples, the apparatus 400 includes a housing 402. In some examples, the housing 402 is formed from a biocompatible material. In various examples, the housing 402 is formed from a metallic material, a polymeric material, a ceramic material, or the like. The apparatus 400, in some examples, includes at least three elongate members, such as, for instance, at least three antennas 406, extending from the housing 402. In some examples, the apparatus 400 includes a first antenna 406A, a second antenna 406B, and a third antenna 406C. In some examples, one or more of the at least three antennas 406 are flexible such that the one or more antennas 406 conform to the body of the patient. However, in other examples, one or more of the at least three antennas 406 can be partially or completely rigid. In some examples, the apparatus 400 need not necessarily include one or more of the at least three antennas and can include another elongate member extending from the housing 402 instead of one or both of the at least three antennas, such as, for example, a lead, a tube, a rod, or a protrusion, to name a few. In some examples, the at least three antennas 406 include different lengths from one another. In some examples, the at least three antennas 406 include similar lengths to one another. In some examples, the apparatus 400 can include more than three antennas 406.

In some examples, the at least three antennas 406 (or other elongate members) include a biocompatible and hermetically sealed connection to circuitry, one or more modules, or one or more electronic components within the housing 402. That is, in some examples, the at least three antennas 406 (or other elongate members) are coupled to the housing 402 to provide electrical engagement between the at least three antennas 406 and the circuitry, one or more modules, or one or more electronic components within the housing 402.

In some examples, the apparatus 400 includes at least three electrodes 408. In some examples, at least a first electrode 408A is disposed on the first antenna 406A, at least a second electrode 408B is disposed on the second antenna 406B, and at least a third electrode 408C is disposed on the third antenna 406C. In some examples, flexible antennas 406 allow the electrodes 408 to be in multiple planes and are not rigidly confined in the same plane. In some examples, the housing 402 can include another electrode, for instance, a fourth electrode. In some examples, the housing 402 is formed from a conductive material, such that the entire housing 402 acts as the fourth electrode. In other examples, the housing 402 is formed from a conductive material and includes a non-conductive and/or insulating coating or other covering around the housing 402 but leaving at least one uninsulated area to act as the fourth electrode. In some examples, the housing 402 includes more than one uninsulated area to act as more than one electrode. In some examples, the housing 402 is formed from a non-conductive material or is completely covered or coated with a non-conductive and/or insulating material and one or more electrodes are affixed or otherwise attached to the housing 402 to form at least the fourth electrode. In some examples, the housing 402 is at least partially coated with a parylene coating, for instance. In some examples, the electrodes 408 of the apparatus 400 include the first electrode 408A at a tip of the first antenna 406A, the second electrode 408B at a tip of the second antenna 406B, and the third electrode 408C at a tip of the third antenna 406C. In some examples, the apparatus 400 can include fewer than three electrodes. In other examples, the apparatus 400 can include more than three electrodes. Although shown in FIG. 4 with one electrode 408 on each the antennas 406, in some examples, it is contemplated that one or more of the antennas can include more than one electrode. In some examples, the antennas 406 can be configured to accommodate multiple electrodes on each antenna. In some examples, electrode pairs on the same antenna 406 can yield local measurements and electrode pairs from different antennas 406 can yield global measurements.

In some examples, the at least three electrodes 408 are disposed in a non-linear configuration. In some examples, as seen in FIG. 4, the first, second, and third electrodes 408A, 408B, 408C generally form a triangle when viewed as shown in FIG. 4, such that three distinct vectors 410 are formed between electrode pairs formed by the first, second, and third electrodes 408A, 408B, 408C. In some examples, the three electrodes 408A, 408B, 408C form the basic Lead I, II, III triangle (Einthoven triangle).

In some examples, the at least three electrodes 408 form at least three vectors 410 along which to sense a physiologic parameter. In some examples, the physiologic parameter includes a cardiac parameter. In further examples, the cardiac parameter includes an electrocardiogram (ECG) signal. In some examples, a first vector 410A is formed between the first electrode 408A and the second electrode 408B, a second vector 410B is formed between the first electrode 408A and the third electrode 408C, and a third vector 410C is formed between the second electrode 408B and the third electrode 408C.

It is to be understood that the apparatuses 100, 200, 300, 400 shown in FIGS. 1-4 are but a few examples of configurations and that other configurations are contemplated herein. For instance, other electrode configurations are contemplated, such as: two or more electrodes on the housing and one on the antenna(s), multiple electrodes on the antenna(s) and the housing, multiple electrodes on the header, or combinations thereof.

In some examples, increased numbers of electrodes are contemplated, thereby creating even larger electrode separation and even more vector options. As more vectors are accommodated, modified vector electrocardiography becomes possible through the implantable device. These multiple antennas could be non-linear, possibly orthogonal, based on the design of the medical device and the headers that accommodate the antennas.

Figure 5:
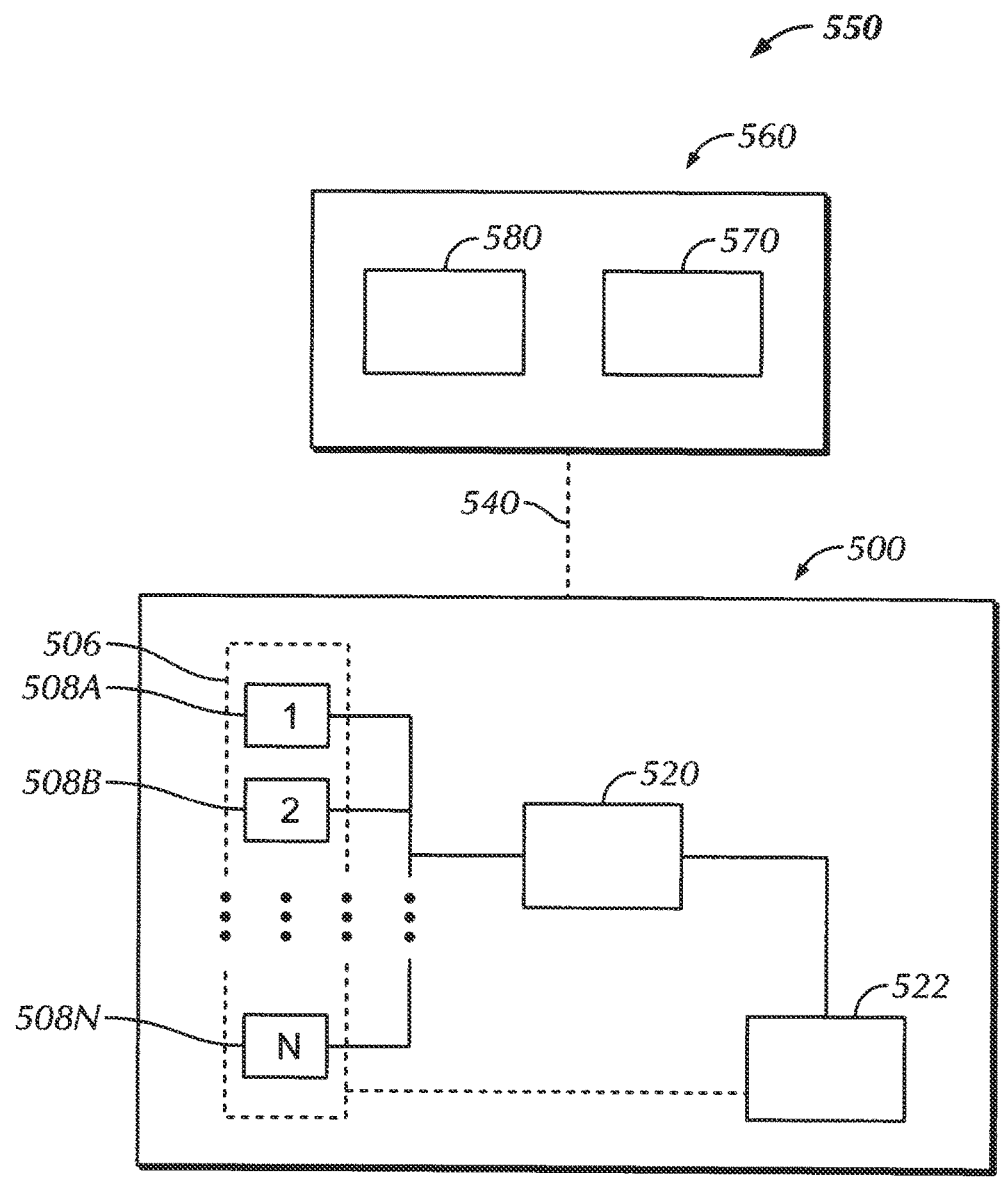
FIG. 5 shows a block diagram of a multi-vector apparatus in accordance with at least one example of the invention.

Referring to FIG. 5, in some examples, a system 550 includes an apparatus 500 is configured for implantation within a body of a patient. In some examples, the apparatus 500 is similar to the apparatuses 100, 200, 300, 400 described herein. In some examples, the apparatus 500 includes an implantable loop recorder (ILR). In some examples, the apparatus 500 can include another type of implantable device. In some examples, the apparatus 500 includes a housing similar to the housings 102, 202, 302, 402 described herein. The apparatus 500, in some examples, includes at least one elongate member, such as, for instance, at least one antenna 506, extending from the housing. In some examples, the at least one antenna 506 is flexible such that the at least one antenna 506 conforms to the body of the patient. However, in other examples, at least one antenna 506 can be partially or completely rigid. In some examples, the at least one antenna 506 (or other elongate member) is electrically coupled between circuitry, one or modules, or one or more electronic components within the housing.

In some examples, the apparatus 500 includes at least three electrodes 508, namely electrodes 508A, 508B, 508C. However, in various examples, more than three electrodes 508A, 508B, . . . 508N is contemplated. It is noted that the antenna 506 in FIG. 5 is shown in phantom around the electrodes 508A, 508B, . . . 508N to denote that one or more of the electrodes 508A, 508B, . . . 508N can be located on the antenna 506 (or on more than one antenna 506) and that one or more of the electrodes 508A, 508B, . . . 508N can be located elsewhere on the apparatus 500 (such as on the housing and/or header), for instance, in configurations similar to those described herein with respect to apparatuses 100, 200, 300, 400. In some examples, at least a first electrode 508A is disposed on the antenna 506 and at least a second electrode 508B is on the housing. In further examples, the apparatus 500 includes a third electrode 508C located on the apparatus 500.

In some examples, the at least three electrodes 508 are disposed in a non-linear configuration. In some examples, the first, second, and third electrodes 508A, 508B, 508C generally form a triangle, such that three distinct vectors are formed between electrode pairs formed by the first, second, and third electrodes 508A, 508B, 508C. In some examples, the three electrodes 508A, 508B, 508C form or approximate the basic Lead I, II, III triangle (Einthoven triangle).

In some examples, the at least three electrodes 508 form at least three vectors along which to sense a physiologic parameter. In some examples, the physiologic parameter includes a cardiac parameter. In further examples, the cardiac parameter includes an electrocardiogram (ECG) signal. In some examples, a first vector is formed between the first electrode 508A and the second electrode 508B, a second vector is formed between the first electrode 508A and the third electrode 508C, and a third vector is formed between the second electrode 508B and the third electrode 508C. In some examples, the signals sensed along the vectors can optionally be processed by a processing module 520. In some examples, all of the electrodes 508A, 508B, . . . 508N feed into the same processing module 520. In further examples, each of the electrodes 508A, 508B, . . . 508N feed into separate processing modules, which are all communicatively coupled together in order to process the signals sensed along the vectors formed by the electrodes 508A, 508B, . . . 508N.

In some examples, the apparatus 500 includes a communications module 522 configured to wirelessly communicate 540 (for instance, using the antenna 506) information (including, but not limited to, the signals sensed, processed and/or unprocessed) to an external device 560. In some examples, the external device 560 includes one or more processing modules 570 (instead of or in addition to the processing module 520 of the apparatus 500) in which various processing of the ECG signals can be performed. In various examples, processing can occur in either the one or more processing modules 570 or the processing module 520 in isolation or in a cooperative or distributive manner between the one or more processing modules 570 and the processing module 520. In some examples, the external device 560 includes an output module 580 configured to output information to a user, including the unprocessed ECG signals and/or the processed signals. The information, in various examples, can be outputted in various ways, including, but not limited to, being shown on a display, printed, emailed, communicated to a computer and/or a database, or a combination thereof. In some examples, the external device includes an input module to allow the user to input information to the system 550, outputted in various ways, including, but not limited to, via a keyboard, touchscreen, or the like. In some examples, the apparatus 500 and/or the external device 560 can include various other modules, circuitry, and/or components, including, but not limited to, one or more of a battery, a battery monitor, a charge control module, a memory module, a filtering module, and amplification module, an analog-to-digital module, and a control module.

Figure 6:
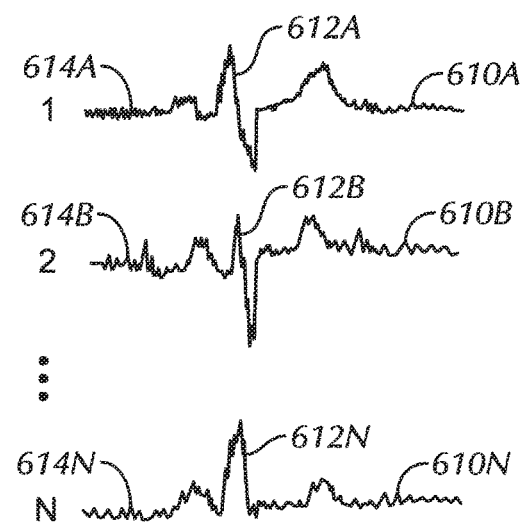
FIG. 6 shows example outputs sensed by a multi-vector apparatus in accordance with at least one example of the invention.

Referring now to FIGS. 5 and 6, in some examples, ECG signals 610A, 610B, . . . 610N (such as those sensed by the apparatus 500) typically include a cardiac component 612A, 612B, . . . 612N and a non-cardiac component 614A, 614B, . . . 614N. The cardiac component 612A, 612B, . . . 612N includes, in some examples, the PQRST complex. In various examples, the non-cardiac component 614A, 614B, . . . 614N can include one or more non-cardiac contributors including, for instance, signal noise, non-cardiac muscle movement, motion by the patient (for instance, walking, running, jumping, etc.), an impact to the patient (for instance, the patient gets hit, falls down, etc.), or the like. In some examples, the ECG signals 610A, 610B, . . . 610N (of each electrode pair) can each be viewed in order to gain diagnostic information that each provides (in a manner similar to a twelve-lead ECG). In further examples, valuable diagnostic information can be provided when all of the ECG signals 610A, 610B, . . . 610N are viewed together.

In some examples, one or more of the ECG signals 610A, 610B, . . . 610N may be poor or otherwise less than optimal, because, for instance, of a localized impact close to an electrode, poor conduction between an electrode and adjacent tissue (for instance, fatty tissue), or movement of an electrode. In some examples, the ECG signals 610A, 610B, . . . 610N can be viewed or analyzed in order to eliminate one or more of the ECG signals 610A, 610B, . . . 610N if deemed poor and/or select one or more of the ECG signals 610A, 610B, . . . 610N for use (such as for analysis, display, trending, storage, etc.). In some examples, electrode pair selection/elimination can be performed manually, for instance, by a doctor or other user viewing the ECG signals 610A, 610B, . . . 610N. In some examples, the system 550 can include an algorithm which continuously or periodically analyzes the ECG signals 610A, 610B, . . . 610N to eliminate and/or select one or more electrode pairs based on the quality of the ECG signals 610A, 610B, . . . 610N. In some examples, the algorithm sweeps through every electrode pair to see which electrodes yield the best readings (for instance, based on signal amplitude, lowest noise, or the like or best representation of a selected ECG feature, to name a few). In this way, the system 550 can automatically switch electrode pairs if the electrode pair being used is no longer giving the best or otherwise desirable readings (for instance, if the device moves within the patient). Such electrode pair selection/elimination can lessen, if not eliminate, the need to perform vector mapping with implantation of the apparatus 500 since the doctor need not determine the "ideal" vector at implantation because the electrode pair can always be switched using either the manual or automatic electrode pair selection/elimination described herein.

In some examples, the system 550 can perform various processing on one or more of the ECG signals 610A, 610B, . . . 610N. In some examples, this processing can be performed using the processing module or circuitry 520 of the apparatus 500 and/or the one or more processing modules 570 of the external device 560. Having multiple electrodes 508, in some examples, permits the use of analytics that leverage the commonality (or differences) between the vectors (such as the ECG signals 610A, 610B, . . . 610N) created by every pair of electrodes 508. While it is possible to do similar techniques using multiple beats over time from one electrode pair, this is only possible when the heart is at or near steady state so that features of sequential beats will match up. If the heart is not at or near steady state, than one beat will be different than another beat from the same electrode pair and features of the beats will not match up. Because beats are not at steady state during most arrhythmias, the apparatus 500 including multiple pairs of electrodes 508 can be advantageous because measuring beats in multiple vectors eliminates the effect of time. That is, the multiple electrodes 508 measuring the same beat at the same time (in different vectors) eliminate the effect of time or variation between beats.

In some examples, since the source signal (in this case the cardiac EGM) is being sensed by the two or more vectors, some of the features of the EGM from the point source can be manipulated to isolate one or more features of the electrical cardiac signal, amplify one or more features of the electrical cardiac signal, or eliminate one or more features of the electrical cardiac signal in the resulting analysis, relative to the rest of the cardiac signal. For instance, in some examples, the multiple vectors can be used to gain or subtract a certain part of the ECG signal, in order to amplify or focus on the remaining part of the ECG signal. In various examples, this can be done in real time to generate a composite strip of the ECG signals or can be done off-line as part of a processed data display. In further examples, this analysis can be done at the level of the implantable apparatus 500 or at the external device 560, such as a personal diagnostic monitor (PDM), for instance.

In some examples, the system 550 can include one or more algorithms to detect a local signal collected from an electrode pair and a far-field signal, which comprises a global signal of cardiac and non-cardiac activity, especially local muscle noise. The one or more algorithms, in some examples, can then subtract the locally-sensed signal from the global signal to allow for a noise free ECG signal. This segregation of signal components can be done based on differentially detected signals rather than (or in addition to) processing aspects of the global signal, such as filtering.

In some examples, dynamic processing of multiple vectors to remove noise or undesirable contribution of movement or myocardial artifact can produce an accurate ECG signal. In some examples, in addition to or instead of filtering and common mode rejection, multi-vector gaining can enable amplification of a specific part of the ECG that is of interest, which can be desirable, for instance, for low amplitude and irregular rhythms that cannot be averaged or filtered through common low/high pass filtering.

Figure 7:
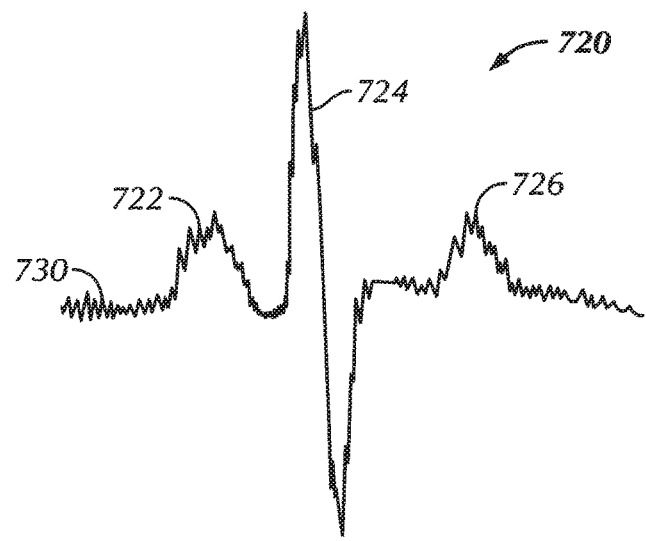
FIG. 7 shows an example of a processed signal from outputs sensed by a multi-vector apparatus in accordance with at least one example of the invention.

In some examples, differential gaining (amplification) and/or common signal (mode) rejection is possible by using two vectors with a common node or electrode 508 thereby allowing for gaining (amplification) or attenuating (subtracting) some of the differences between the two pairs of electrode 508. In some examples, the apparatus 500 simultaneously acquires the ECG signals 610A, 610B, . . . 610N from the multiple vectors using a common electrode 508 as a node. In some examples, common elements of the ECG signals 610A, 610B, . . . 610N (like the QRS complex, P-wave, and/or T-wave, for example) can be sensed relative to the baseline noise inherent to the ECG signals 610A, 610B, . . . 610N from each pair of electrode 508. In some examples, two of more of the ECG signals 610A, 610B, . . . 610N can be point-by-point multiplied to yield a processed ECG signal 720, as seen in FIG. 7, in which a P wave 722, a QRS complex 724, and a T wave 726 are more pronounced than in the individual ECG signals 610A, 610B, . . . 610N and noise 730 in the processed ECG signal 720 is less pronounced (a signal-to-noise ratio of the processed ECG signal 720 is less than signal-to-noise ratios of the ECG signals 610A, 610B, . . . 610N), In some examples, random noise characteristics can be amplified by subtracting out the high amplitude common features from the ECG signals 610A, 610B, . . . 610N derived from two vectors in order to isolate the lower amplitude background features of a given signal.

Figure 8:
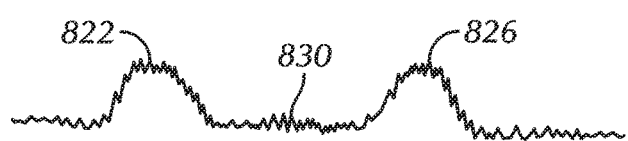
FIG. 8 shows an example of a processed signal from outputs sensed by a multi-vector apparatus in accordance with at least one example of the invention.

In some examples, multiple ECG signals 610A, 610B, . . . 610N from multiple electrodes 508 allows for gaining and/or subtracting of one or more parts of a signal to augment one or more others. For instance, in some examples, two or more of the ECG signals 610A, 610B, . . . 610N can be used to essentially eliminate or attenuate a QRS complex of a processed ECG signal 820, as seen in FIG. 7, leaving a T wave 826 (an ischemia indicator and an alternans indicator, for instance) and a P wave 822 (an atrial fibrillation indicator and an atrial flutter indicator, for instance) for analysis, viewing, or otherwise using by the doctor or other user. In further examples, noise 830 in the processed ECG signal 820 can be attenuated, as described herein. While such an example is shown in FIG. 8, it is not intended to be limiting. That is, in other examples, it is contemplated that gaining and/or subtracting can be used to eliminate or augment any feature of the ECG signals 610A, 610B, . . . 610N.

Figure 11:
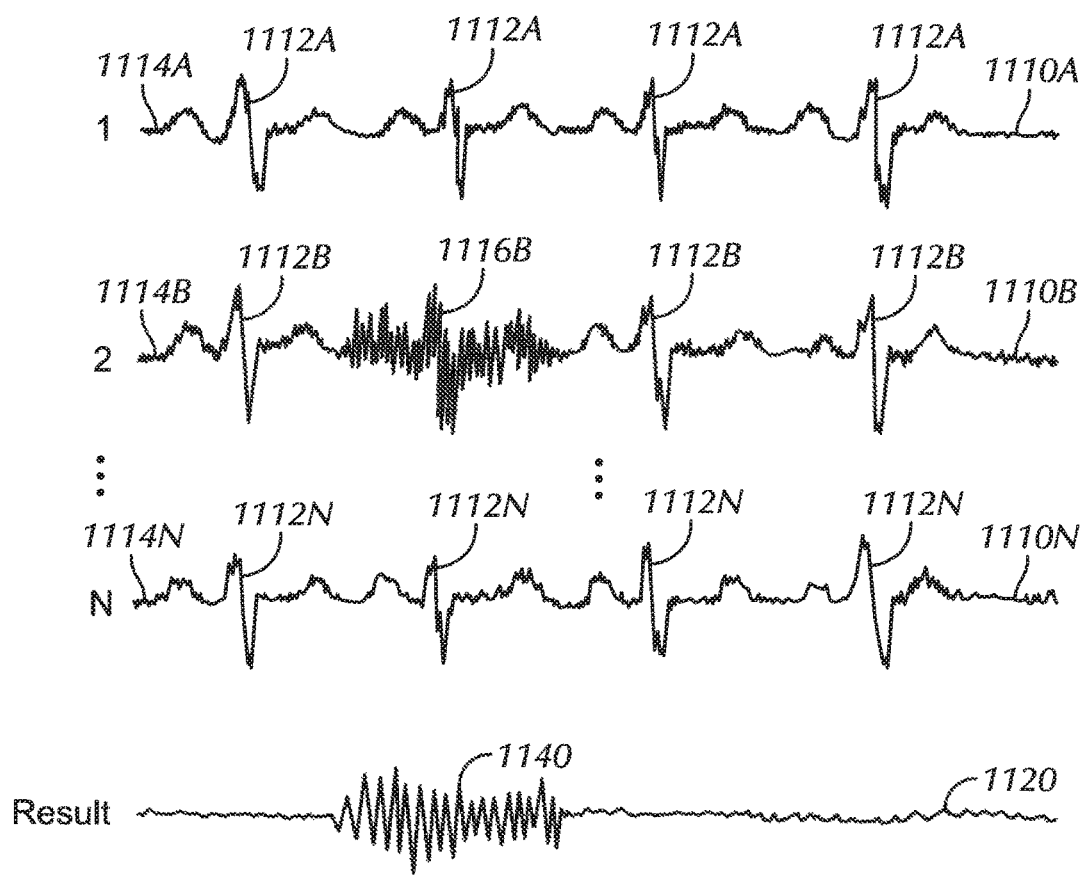
FIG. 11 shows example outputs sensed by a multi-vector apparatus and a processed signal from the outputs in accordance with at least one example of the invention.

In some examples, multiple electrodes 508 sense things differently. Because the system 550 uses multiple vectors, in some examples, even the same point source signal, such as from the heart, will look different when viewed from different pairs of electrodes 508, thereby allowing for a differential read of the ECG signals 610A, 610B, . . . 610N due to the vector differences. In some examples, if one pair of electrodes 508 senses a local signal (such as a localized EMG like a skeletal muscle twitch, for instance), the vectors from one or more of the other pairs of electrodes 508 may not register a similar noise feature. In such examples, the differences between the multiple vectors can be used to amplify the cardiac signal relative to the local noise or amplify the noise relative to the cardiac signal, depending on the application. For instance, in some examples, a processed ECG signal 1120, as shown in FIG. 11, can include processed local noise 1140 that is amplified relative to a cardiac signal. ECG signals 1110A, 1110B, . . . 1110N each include cardiac components 1112A, 1112B, . . . 1112N and non-cardiac components 1114A, 1114B, . . . 1114N. However, only the ECG signal 1110B includes local noise 1116B. Using the differences between the multiple vectors the local noise 1116B can be amplified relative to the cardiac signal so that the processed local noise 1140 can be focused on in the processed ECG signal 1120.

Figure 9A:
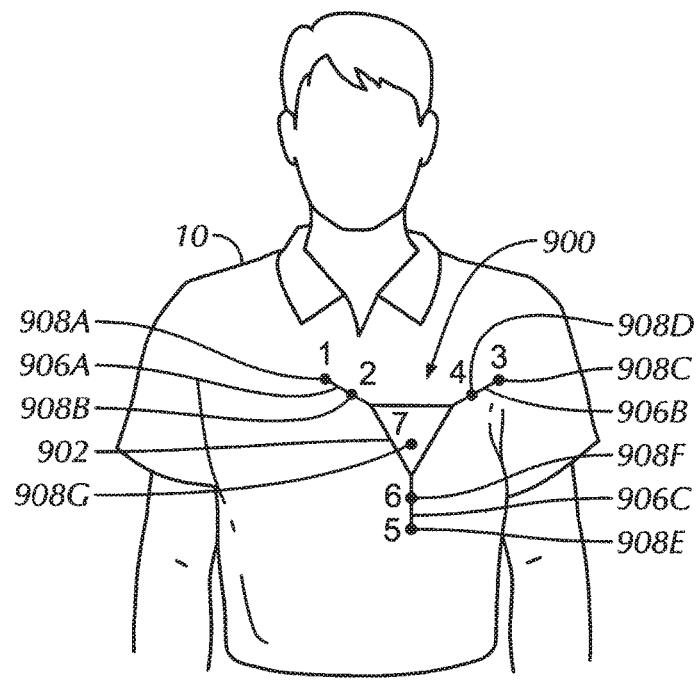
FIGS. 9A-9C show example configurations of multi-vector implantable apparatuses in accordance with examples of the invention.

Referring to FIG. 9A, in some examples, an implantable apparatus 900 is depicted implanted within a body of a patient 10. In some examples, the apparatus 900 is similar to the apparatuses 100, 200, 300, 400, 500 described herein. Although the apparatus 900 is similar in appearance to the apparatus 400 of FIG. 4, it is not intended to be so limited, as the apparatus 900, in various examples, can take a form similar to any one of the apparatuses 100, 200, 300, 400, 500 or a form that is different from any of apparatuses 100, 200, 300, 400, 500. In some examples, the apparatus 900 includes an implantable loop recorder (ILR). In some examples, the apparatus 900 can include another type of implantable device. In some examples, the apparatus 900 is configured to communicate or otherwise work with an external device, for instance, similar to the external device 560 of FIG. 5. In some examples, the apparatus 900 (and/or the external device) is configured to employ one or more algorithms to allow the apparatus 900 (and/or the external device) to process multi-vector signals, as described herein.

In some examples, the apparatus 900 includes a housing 902. The apparatus 900, in some examples, includes three antennas 906, namely a first antenna 906A, a second antenna 906B, and a third antenna 906C. In other examples, the apparatus can include fewer or more than three antennas. In some examples, the apparatus includes seven electrodes 908, although it is contemplated that, in other examples, the apparatus can include more or fewer than seven electrodes. In this example, first and second electrodes 908A, 908B are disposed on the first antenna 906A; third and fourth electrodes 908C, 908D are disposed on the second antenna 906B; fifth and sixth electrodes 908E, 908F are disposed on the third antenna 906C; and a seventh electrode 908G is disposed on the housing 902. In other examples, it is contemplated that any one or more of the antennas 906 can include more or less than two electrodes 908 and/or that the housing 902 can include more or less than one electrode 908.

Figures 9B, 9C:
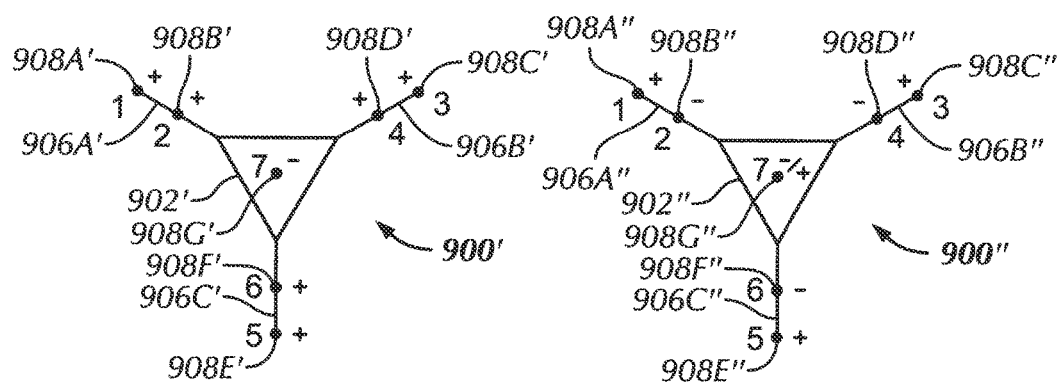

In some examples, a vector is created between two electrodes 908 of opposite polarities. That is, one electrode 908 of a pair includes a positive polarity, and the other electrode 908 of the pair includes a negative polarity. FIGS. 9B and 9C show two example pairing/polarity configurations of the apparatus 900, a first example configuration 900' shown in FIG. 9B with numbering including a single prime (') and a second example configuration 900" shown in FIG. 9C with numbering including a double prime (").

Referring first to the first example configuration 900' of FIG. 9B, each of the first, second, third, fourth, fifth, and sixth electrodes 908A', 908B', 908C', 908D', 908E', 908F' includes a positive polarity and the seventh electrode 908G' includes a negative polarity, such that six electrode pairs can be formed (for instance, between the first and seventh electrodes 908A', 908G'; between the second and seventh electrodes 908B', 908G', etc.).

Referring now to the second example configuration 900" of FIG. 9C, each of the first, third, and fifth electrodes 908A", 908C", 908E" includes a positive polarity; each of the second, fourth, and sixth electrodes 908B", 908D", 908F" includes a negative polarity; and the seventh electrode 908G" is configured to switch polarities. In this way, the seventh electrode 908G" with a negative polarity can pair with any of the first, third, and fifth electrodes 908A", 908C", 908E", and the seventh electrode 908G" with a positive polarity can pair with any of the second, fourth, and sixth electrodes 908B", 908D", 908F". Additionally, in some examples, local bipoles can be formed with the electrodes 908" of each the antennas 906" (namely, a first local bipole formed by the first and second electrodes 908A", 908B"; a second local bipole formed by the third and fourth electrodes 908C", 908D"; and a third local bipole formed by the fifth and sixth electrodes 908E", 908F") to sense, for instance local fields. In some examples, global electrode pairs can be used to sense global fields, for instance, using one electrode 908" on one antenna 906" and another electrode 908" on another antenna 906" or the seventh electrode 908G" on the housing 902".

As can be seen, the first and second example configurations 900', 900" provide numerous vectors along which to sense, for instance, ECG signals in order to better understand cardiac functioning of a patient. In other examples, other polarity configurations are contemplated. In some examples, the apparatus 900 can be configured to switch the polarity of one or more of the electrodes 908, manually (by a doctor or other user) and/or automatically (by a module, circuitry, and/or algorithm of the apparatus 900 or the external device).

Figure 10:
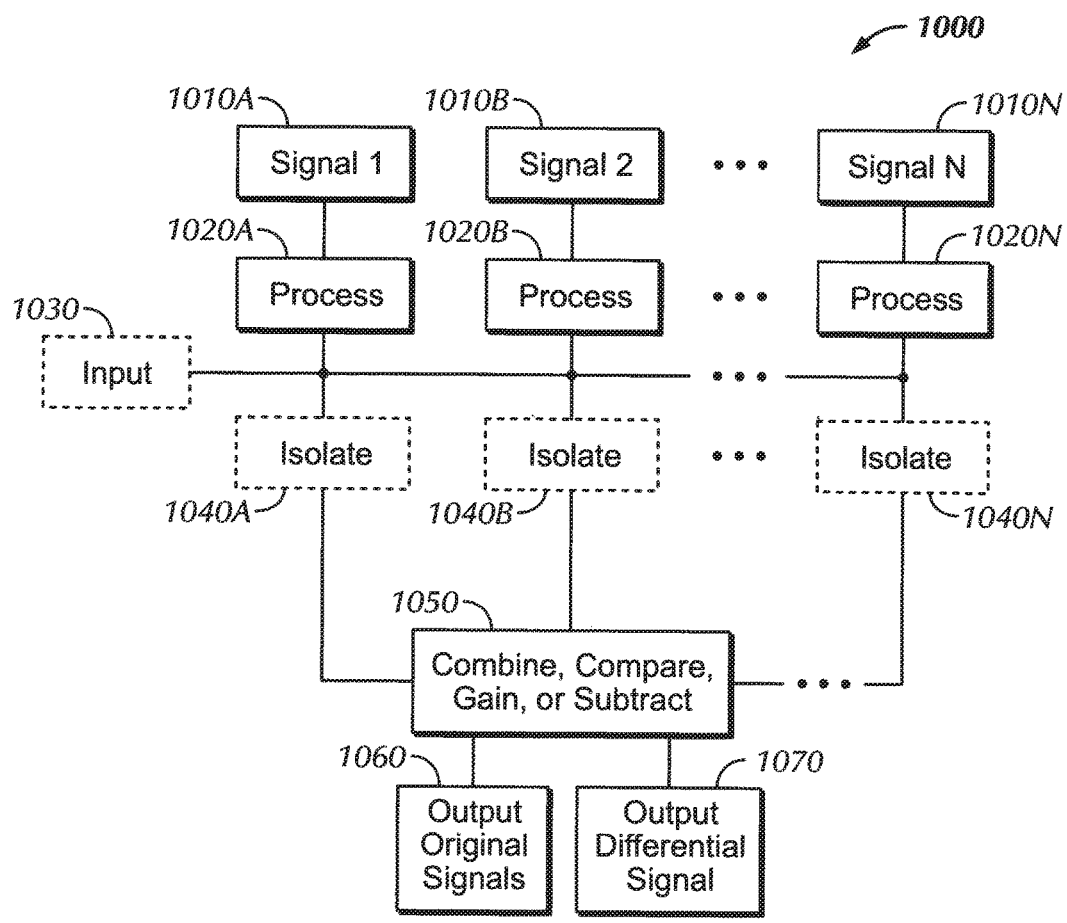
FIG. 10 shows an example flowchart of steps to output a differential signal accordance with at least one example of the invention.

Referring to FIG. 10, in some examples, a method 1000 for processing multi-vector signals can be used, for instance, with apparatuses 100, 200, 300, 400, 900 and/or system 550. In some examples, signals 1010A, 1010B, . . . 1010N are collected across multiple electrode pairs. In some examples, each of the signals 1010A, 1010B, . . . 1010N can be processed 1020A, 1020B, . . . 1020N as described herein. In some examples, a doctor or other user can input 1030 (for instance, using the input module of the external device 560 of the system 550) one or more signal features, time periods, etc. to isolate 1040A, 1040B, . . . 1040N. In some examples, differential processing (for instance, combining, comparing, gaining, and/or subtracting) is performed in manners similar to those described herein. In some examples, the method 1000 can output 1060 the original signals 1010A, 1010B, . . . 1010N and/or output 1070 the differential signal (such as, for instance, processed signals 720, 820, 1120). In some examples, outputting 1060, 1070 can be performed using the output module 580 of the external device 560 of the system 550.

Referring to FIGS. 12A-12E, in some examples, an implantable apparatus 1200 is depicted implanted within a body of a patient 10. In some examples, the apparatus 1200 is similar to the apparatuses 100, 200, 300, 400, 500, 900 described herein. Although the apparatus 1200 is similar in appearance to the apparatus 400 of FIG. 4 and apparatus 900 of FIG. 9A, it is not intended to be so limited. In some examples, the apparatus 1200 includes an implantable loop recorder (ILR). In some examples, the apparatus 1200 can include another type of implantable device. In some examples, the apparatus 1200 is configured to communicate or otherwise work with an external device, for instance, similar to the external device 560 of FIG. 5. In some examples, the apparatus 1200 (and/or the external device) is configured to employ one or more algorithms to allow the apparatus 1200 (and/or the external device) to process multi-vector signals, as described herein. In some examples, the apparatus 1200 includes a housing 1202. The apparatus 1200, in some examples, includes three antennas 1206, namely a first antenna 1206A, a second antenna 1206B, and a third antenna 1206C. Although not shown, the apparatus 1200 includes multiple electrodes, such as one or more electrodes on each of the antennas 1206 and one or more electrodes on the housing 1202.

Figure 12A:
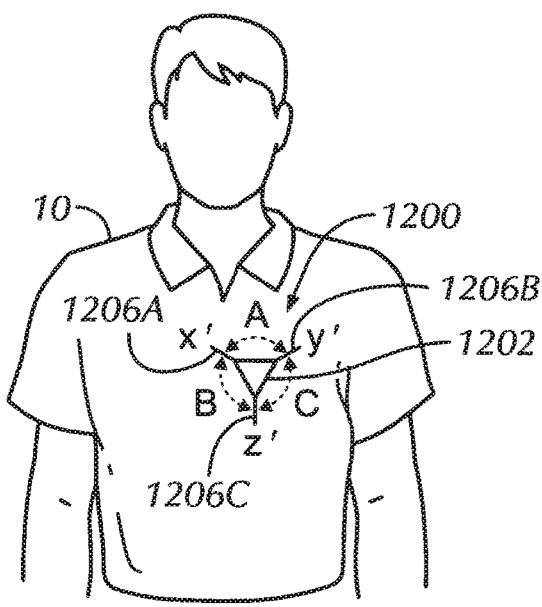
FIG. 12A shows a multi-vector implantable apparatus in accordance with at least one example of the invention.
Figure 12B:
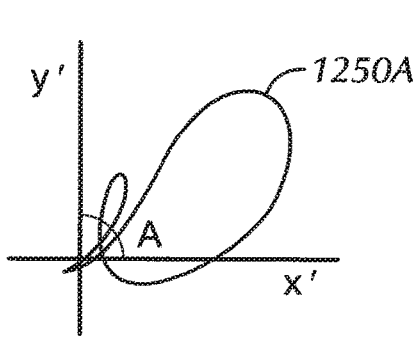
FIGS. 12B-12D show two-dimensional vector maps from the multi-vector implantable apparatus of FIG. 12A.
Figure 12C:
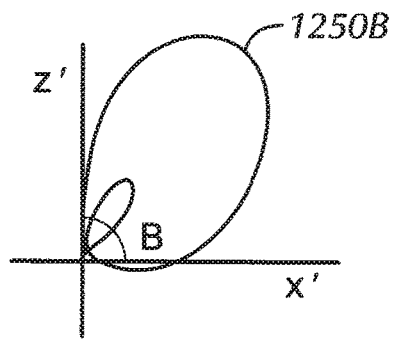
Figure 12D:
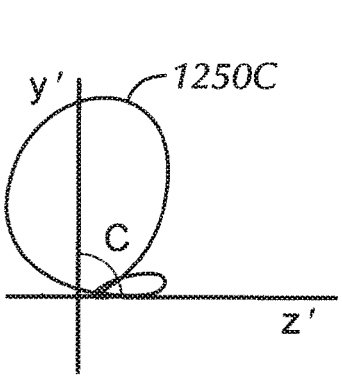
Figure 12E:
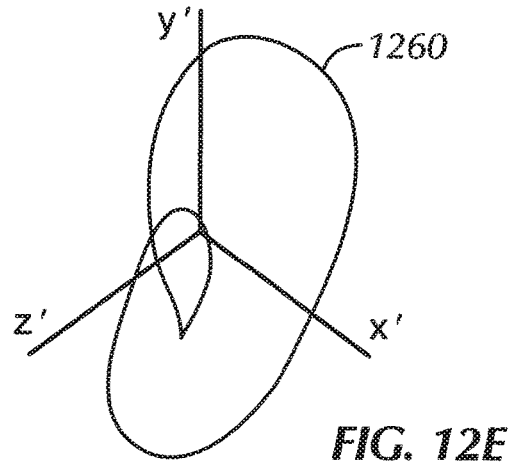
FIG. 12E shows a three-dimensional vector maps from the multi-vector implantable apparatus of FIG. 12A.

In some examples, the apparatus 1200 can be used for vector electrocardiography. Typical vector electrocardiography includes electrodes disposed such that a ninety-degree Cartesian system is formed. Because such a configuration may be difficult to achieve with the implantable apparatus 1200, in some examples, a surrogate coordinate system can be used based on conformation to the body of the patient 10 of the antennas 1206 and an implanted geometry of the electrodes of the apparatus 1200. That is, in some examples, the axes of the surrogate coordinate system can be based on the conformal electrodes and where they are implanted in the subcutaneous space of the patient 10. For instance, in some examples, the first antenna 1206A and associated electrode(s) can form an x' axis, the second antenna 1206B and associated electrode(s) can form a y' axis, and the third antenna 1206C and associated electrode(s) can form a z' axis. In some examples, an angle A is disposed between the x' axis and the y' axis, an angle B is disposed between the x' axis and the z' axis, and an angle C is disposed between the y' axis and the z' axis. Using such a geometry, in some examples, the surrogate coordinate system can be formed and vectors mapped over time. The apparatus 1200 (and/or the external device), in some examples, can be configured to algorithmically determine and map vectors of the electric field. In some examples, the apparatus 1200 (and/or the external device) can map and/or display one or more two-dimensional vector maps, such as a first vector map 1250A along an x'-y' plane (FIG. 12B), a second vector map 1250B along an x'-z' plane (FIG. 12C), and/or a third vector map 1250C along a y'-z' plane (FIG. 12D). In some examples, the apparatus 1200 (and/or the external device) can map and/or display each of the two-dimensional vector maps 1250A, 1250B, 1250C combined into a three-dimensional vector map 1260 (FIG. 12E). In this way, in some examples, the apparatus 1200 (and/or the external device) can derive a vector map showing how the cardiac electrical field is operating, which can then be used for diagnostic or other purposes by a doctor or other user.

The present inventors have recognized various advantages of the subject matter described herein. For instance, in some examples, the apparatuses, systems, algorithms, and methods described herein can be used to collect multiple ECG signals along multiple vectors to enhance analysis of the ECG signal and better understand cardiac functioning of a patient. In various examples, the apparatuses, systems, algorithms, and methods described herein are considered advantageous in that they allow for accentuation or attenuation of various features of an ECG signal to allow for easier and/or better analysis of a processed ECG signal. Additionally, in various examples, the apparatuses, systems, algorithms, and methods described herein include the ability, manually and/or automatically, to select/eliminate electrode pairs based on, for instance, signal quality. While various advantages of the example apparatuses, systems, methods, and algorithms are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment.

The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein," Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. An apparatus configured for implantation within a body of a patient, the apparatus comprising:
    a housing;
    at least two antennas extending from the housing, including a first antenna and a second antenna, the first and second antennas being flexible such that the first and second antennas conform to the body of the patient;
    at least three electrodes, wherein at least a first electrode is disposed on the first antenna, at least a second electrode is disposed on the housing, and at least a third electrode is disposed on the second antenna, wherein the first, second, and third electrodes are disposed in a non-linear configuration and provide at least three vectors along which to sense an electrocardiogram (ECG) signal; and
    circuitry configured to use the at least three vectors to gain or subtract a first portion of the ECG signal and amplify a remaining second portion of the ECG signal.

2. The apparatus of claim 1, wherein the first antenna includes at least two electrodes including the first electrode and a fourth electrode.

3. The apparatus of claim 2, wherein the at least two electrodes of the first antenna are configured to measure a local signal and the first electrode and the second electrode are configured to measure a global signal.

4. The apparatus of claim 1, comprising a header attached to the housing, wherein the at least two antennas are coupled to the header.

5. The apparatus of claim 4, wherein at least a fourth electrode is disposed on the header.

6. A system comprising:
    an implantable device configured for implantation within a body of a patient, the device including:
    a housing;
    at least two antennas extending from the housing including a first antenna and a second antenna, the first and second antennas being flexible such that the first and second antennas conform to the body of the patient;
    at least three electrodes, wherein at least a first electrode is disposed on the first antenna, at least a second electrode is disposed on the housing, and at least a third electrode is disposed on the second antenna, wherein the first, second, and third electrodes are disposed in a non-linear configuration and provide at least three vectors along which to sense an electrocardiogram (ECG) signal;
    an external device communicatively coupled to the implantable device; and
    circuitry configured to use the at least three vectors to gain or subtract a first portion of the ECG signal and amplify a remaining second portion of the ECG signal, wherein the circuitry is disposed within one of the implantable device and the external device.

7. The system of claim 6, wherein the implantable device includes a header attached to the housing, wherein the at least two antennas are coupled to the header.

8. The system of claim 7, wherein at least a fourth electrode is disposed on the header.

9. The system of claim 6, wherein the first antenna includes at least two electrodes including the first electrode and a fourth electrode.

10. The system of claim 9, wherein the system is configured to:
    measure a local signal between the first electrode and the fourth electrode of the first antenna; and
    measure a global signal between:
        the first electrode of the first antenna and the second electrode of the housing; or
        the first electrode of the first antenna and the third electrode of the second antenna.

11. An apparatus configured for implantation within a body of a patient, the apparatus comprising:
    a housing;
    at least two antennas extending from the housing, including a first antenna and a second antenna, the first and second antennas being flexible such that the first and second antennas conform to the body of the patient;
    at least three electrodes, wherein at least a first electrode is disposed on the first antenna, at least a second electrode is disposed on the housing, and at least a third electrode is disposed on the second antenna, wherein the first, second, and third electrodes are disposed in a non-linear configuration and provide at least three vectors along which to sense an electrocardiogram (ECG) signal; and
    circuitry configured to use the at least three vectors to determine a local signal and a global signal, the circuitry being configured to subtract the local signal from the global signal to decrease an amount of noise present in the ECG signal.

12. The apparatus of claim 11, wherein the first antenna includes at least two electrodes including the first electrode and a fourth electrode.

13. The apparatus of claim 12, wherein the at least two electrodes of the first antenna are configured to measure a local signal and the first electrode and the second electrode are configured to measure a global signal.

14. The apparatus of claim 11, comprising a header attached to the housing, wherein the at least two antennas are coupled to the header.

15. The apparatus of claim 14, wherein at least a fourth electrode is disposed on the header.

16. A system comprising:
    an implantable device configured for implantation within a body of a patient, the device including:
    a housing;

at least two antennas extending from the housing including a first antenna and a second antenna, the first and second antennas being flexible such that the first and second antennas conform to the body of the patient;

at least three electrodes, wherein at least a first electrode is disposed on the first antenna, at least a second electrode is disposed on the housing, and at least a third electrode is disposed on the second antenna, wherein the first, second, and third electrodes are disposed in a non-linear configuration and provide at least three vectors along which to sense an electrocardiogram (ECG) signal;

an external device communicatively coupled to the implantable device; and circuitry configured to use the at least three vectors to determine a local signal and a global signal, the circuitry being configured to subtract the local signal from the global signal to decrease an amount of noise present in the ECG signal, wherein the circuitry is disposed within one of the implantable device and the external device.

17. The system of claim 16, wherein the implantable device includes a header attached to the housing, wherein the at least two antennas are coupled to the header.

18. The system of claim 17, wherein at least a fourth electrode is disposed on the header.

19. The system of claim 16, wherein the first antenna includes at least two electrodes including the first electrode and a fourth electrode.

20. The system of claim 19, wherein the system is configured to:
measure a local signal between the first electrode and the fourth electrode of the first antenna; and
measure a global signal between:
the first electrode of the first antenna and the second electrode of the housing; or
the first electrode of the first antenna and the third electrode of the second antenna.

* * * * *